United States Patent [19]

Kageyama et al.

[11] Patent Number: 5,055,413
[45] Date of Patent: Oct. 8, 1991

[54] METHOD OF MEASURING IMPURITIES IN OXIDE FILMS USING A MELTABLE SAMPLE COLLECTION STICK

[75] Inventors: Mokuji Kageyama, Yokohama; Ayako Maeda, Kawasaki, both of Japan

[73] Assignee: Kabushiki Kaisha Toshiba, Kawasaki, Japan

[21] Appl. No.: 338,797

[22] Filed: Apr. 17, 1989

[30] Foreign Application Priority Data

Apr. 25, 1988 [JP] Japan ................................ 63-102198

[51] Int. Cl.$^5$ ........................... G01N 1/00; G01N 1/34
[52] U.S. Cl. .................................. 436/178; 436/177; 436/174
[58] Field of Search ............... 436/174, 177, 178, 181, 436/5; 422/68.1, 69; 73/863.11, 864

[56] References Cited

U.S. PATENT DOCUMENTS

| | | | |
|---|---|---|---|
| 4,144,760 | 3/1979 | Schlueter et al. | 73/864.71 |
| 4,584,886 | 4/1986 | Matsunaga et al. | |
| 4,634,497 | 1/1987 | Shimazaki. | |
| 4,990,459 | 2/1991 | Maeda et al. | 436/174 |

FOREIGN PATENT DOCUMENTS 1211010 11/1970 United Kingdom .

OTHER PUBLICATIONS

Japanese Journal of Applied Physics—Supplements, 16th (1984 International) Conference on Solid State Devices and Materials, Kobe, 1984; "Chemical Analysis of Ultratrace Impurities in SiO$_2$ Films", Shimazaki et al., pp. 281-284.

Ramirez-Munoz, J., Atomic-Absorption Spectrocopy and Analysis by Atomic-Absorption Flame Photometry, Elsevier Publishing Co., 1968, pp. 11-14.

*Primary Examiner*—David L. Lacey
*Assistant Examiner*—Jan M. Ludlow
*Attorney, Agent, or Firm*—Finnegan, Henderson, Farabow, Garrett, and Dunner

[57] ABSTRACT

An object to be measured is moved relative to a stick prepared by cooling and solidifying a solution into a rod-like shape. The stick is brought into contact with the surface of the object to be measured, thereby dissolving a natural oxide film and the like formed on the surface of the object. After the stick is brought into contact with the overall surface of the object to be measured, the solution held at the end portion of the stick is analyzed by chemical analysis to measure the type and amount of an impurity adhered on the surface of the object.

2 Claims, 1 Drawing Sheet

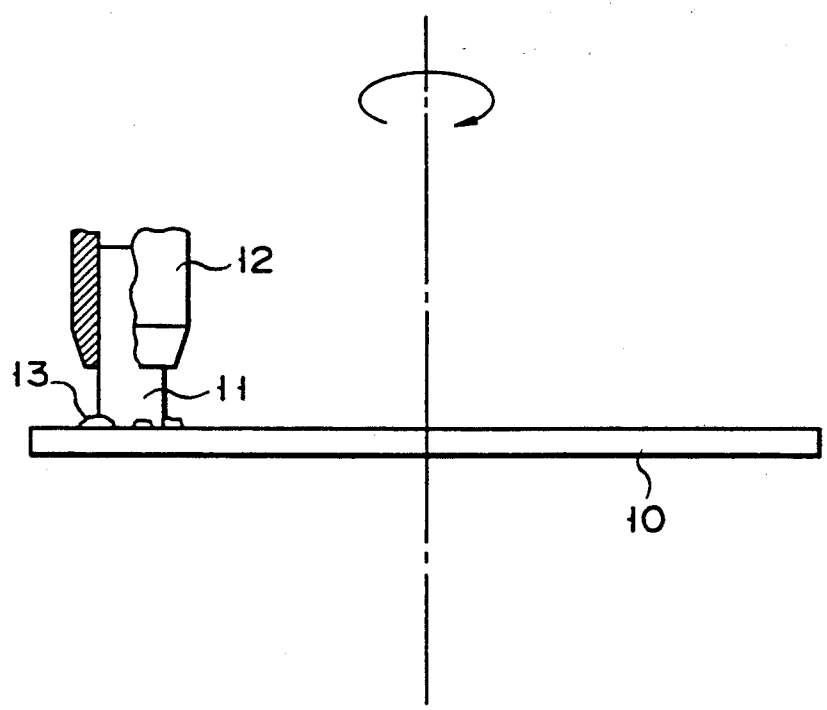
F I G. 1

METHOD OF MEASURING IMPURITIES IN OXIDE FILMS USING A MELTABLE SAMPLE COLLECTION STICK

BACKGROUND OF THE INVENTION

1. Field of the Invention

The present invention relates to an impurity measuring method of measuring the type and amount of an impurity adhered on the surface of an object to be measured, especially, a semiconductor substrate.

2. Description of the Related Art

It is well known that when an impurity such as sodium (Na), potassium (K) or iron (Fe) is contained in a thin film, e.g., an oxide film formed on a semiconductor substrate, electrical characteristics of a semiconductor element are significantly adversely affected, even if the amount of the impurity is very small. Therefore, in order to improve the electrical characteristics of the semiconductor element, mixing of the impurity from the substrate surface must be reduced as much as possible. For this purpose, the degree of contamination on the substrate surface must be correctly analyzed and measured.

The degree of contamination on the substrate surface is conventionally measured by using secondary ion mass spectrometry, Auger spectroscopic analysis or neutron activation analysis. Since these methods require a large-scale, expensive measuring instrument, the analysis cost is high. In addition, skill is required for the analyzing operation. Also, since each analyzing method uses an electron beam or a light beam, local analysis can be performed, but the degree of contamination on the overall surface cannot be estimated.

For this reason, in place of the above instrumental analyzing methods, a method of easily measuring the degree of contamination on the overall substrate surface is proposed. In this method, an oxide film having a predetermined thickness is formed beforehand on the surface of a substrate and dissolved by using a hydrofluoric acid vapor, and the resultant solution is recovered to measure an impurity by using a spectroscopic analyzer. This method is called vapor phase cracking.

The above method, however, requires an oxide film formation step. In this oxide film formation step, an impurity is mixed from an oxidation atmosphere into an oxide film, the impurity evaporates from the substrate surface into the oxidation atmosphere, or the impurity contained in the substrate is diffused to the surface. For this reason, this method is undesirable in terms of reliability in analysis values.

In another conventional method, without forming an oxide film on the surface of a substrate by an oxidation step, the overall substrate is dipped in a hydrofluoric acid solution to dissolve a natural oxide film naturally formed on the substrate surface, and the resultant solution is recovered to measure an impurity amount by using a spectroscopic analyzer.

In this method, however, since an extremely large amount of the hydrofluoric acid solution is required for recovering the impurity, the concentration of the impurity contained in the solution is significantly decreased, and therefore analysis sensitivity and precision are degraded. In addition, according to this method, the hydrofluoric acid solution is contaminated by the impurity adhered on a vessel with very high probability.

SUMMARY OF THE INVENTION

It is an object of the present invention to provide an impurity measuring method which can measure an amount of an impurity adhered to the surface of an object to be measured with high sensitivity and precision and which provides low analysis cost and high reliability.

An impurity measuring method of the present invention is characterized in that a stick obtained by cooling and solidifying a solution into a rod-like shape is brought into contact with the surface of an object to be measured. The stick and the object to be measured are moved relative to each other, thereby dissolving a natural oxide film formed on the surface of the object to be measured. An impurity scattered on the surface of the object to be measured is recovered while the solution is held at the distal end portion of the stick. After the stick is brought into contact with the overall surface of the object to be measured, the solution recovered at the distal end portion of the stick is analyzed, thereby measuring an amount of the impurity adhered on the surface of the object to be measured.

In the measuring method of the present invention, the stick is kept in contact with the surface of the object to be measured to give a relative movement between the stick and the object to be measured. Therefore, dissolution of the natural oxide film formed on the surface of the object to be measured and recovery of the resultant solution can be simultaneously performed.

In addition, since the recovered solution is not brought into contact with anything but the surface of the object to be measured, only the natural oxide film containing the impurity on the surface of the object to be measured is dissolved in the solution. Therefore, a highly reliable measurement can be performed with high sensitivity and precision by using the solution having a proper amount of acid and a sufficient impurity concentration for analysis.

According to the present invention, there is provided an impurity measuring method which can measure an impurity adhered on an object to be measured with high sensitivity and precision and which realizes a low measurement cost and high reliability.

BRIEF DESCRIPTION OF THE DRAWINGS

FIG. 1 is a view showing an arrangement of an apparatus used for carrying out a method of the present invention.

DETAILED DESCRIPTION OF THE PREFERRED EMBODIMENTS

An embodiment of the present invention will be described in detail below with reference to the accompanying drawing.

FIG. 1 shows an apparatus for carrying out a method of the present invention. A silicon semiconductor substrate 10, as an object to be measured, is placed on a support table (not shown) and horizontally rotated together with the support table. A stick 11 is brought into contact with the surface of the rotating substrate 10.

The stick 11 is prepared by cooling and solidifying a solution, for dissolving a natural oxide film containing an impurity adhered on the substrate surface and having a hydrophobic nature with respect to the substrate surface, into a rod-like shape. An example of the solution is a hydrofluoric acid (HF) solution having a concentration of 0.5% to 2%.

The stick 11 is chucked and held by a chuck 12 so that its distal end portion is brought into contact with the surface of the substrate 10. The chuck 12 is driven so that the stick 11 horizontally moves from the periphery of the substrate 10 toward the center of rotation or vice versa.

In such an apparatus, the stick 11 is sequentially dissolved by:
(1) intersurface pressure between the stick and the substrate surface induced upon rotation of the substrate 10;
(2) a chemical reaction between the stick and the oxide film or the like on the substrate surface; and
(3) heating of the substrate 10.

A solution 13 wets the substrate surface and the substrate surface maintains its hydrophilic nature while the natural oxide film (not shown) formed on the substrate surface in contact with the solution 13 is present. When the natural oxide film is dissolved by the solution 13, however, fluorine (F) adheres on the substrate surface to increase a hydrophobic nature. For this reason, the solution 13 is repelled by the substrate surface. Meanwhile, the solution 13 is kept hydrophilic with respect to the stick 11. Therefore, the solution 13 is held around the distal end portion of the stick 11 and moved with the stick 11.

When the stick 11 is brought into contact with the overall surface of the substrate 10 to dissolve the natural oxide film, the impurity scattered on the substrate surface is recovered together with the solution 13 at the distal end portion of the stick 11. Thereafter, the recovered solution 13 is sampled and analyzed by chemical analysis using a spectroscopic analyzer to measure the type and amount of the impurity, thereby determining a degree of contamination of the substrate 10.

Since the above method according to the embodiment of the present invention does not require an expensive measuring instrument, measurement cost can be decreased. In addition, the stick 11 is kept in contact with the surface of the substrate 10. Therefore, dissolution of the natural oxide film formed on the substrate surface and recovery of the solution 13 can be simultaneously performed, thereby reducing measurement time.

The recovered solution 13 is not brought into contact with anything but the substrate surface, and, therefore, only the natural oxide film containing the impurity on the substrate surface is dissolved therein. Since the solution 13 has a proper amount of acid and a sufficient impurity concentration for analysis, highly reliable measurements can be performed with high sensitivity and precision upon chemical analysis using a spectroscopic apparatus.

The present invention is not limited to the above embodiment, but can be modified. For example, in the above embodiment, the present invention is applied to measurement of an impurity on the surface of a semiconductor substrate. The method of the present invention, however, can be applied to general measurement of a degree of contamination on the surface of a metal. In addition, the type of the solution constituting the stick can be selected in accordance with the type of object material. Examples of the solution constituting the stick are
(1) HF
(2) $HF + HNO_3$
(3) $HF + H_2O_2$
(4) $HCl + H_2O_2$ Furthermore, when the stick is to be brought into contact with the surface of an object to be measured, the object to be measured may be heated to accelerate dissolution of the stick.

What is claimed is:
1. A method of measuring a surface impurity in an oxide film comprising the steps of:
contacting a stick comprising a material that will dissolve an oxide film and will melt with a surface comprising an oxide film;
moving said stick along said surface, wherein a portion of the stick that is in contact with the surface is melted and said melted portion dissolves an impurity from the oxide film and adheres to the stick during movement along the surface; and
recovering and analyzing said melted portion to measure the type and amount of said impurity.
2. A method according to claim 1, wherein said material is a solution containing reagents selected from the group consisting of HF, $HF + NHO_3$, $HF + H_2O_2$, and $HCl + H_2O_2$.

* * * * *